(12) United States Patent
Jin et al.

(10) Patent No.: US 8,202,555 B2
(45) Date of Patent: Jun. 19, 2012

(54) NATURAL PHARMACEUTICAL PREPARATIONS FOR INCREASING ALBUMIN

(76) Inventors: Zheming Jin, Shanghai (CN); Xitian Zhang, Shanghai (CN)

( * ) Notice: Subject to any disclaimer, the term of this patent is extended or adjusted under 35 U.S.C. 154(b) by 177 days.

(21) Appl. No.: 12/793,958

(22) Filed: Jun. 4, 2010

(65) Prior Publication Data

US 2011/0033556 A1 Feb. 10, 2011

(30) Foreign Application Priority Data

Aug. 7, 2009 (CN) .......................... 2009 1 0162497

(51) Int. Cl.
*A01N 65/00* (2009.01)
(52) U.S. Cl. ........................................................ 424/725
(58) Field of Classification Search .................. None
See application file for complete search history.

(56) References Cited

FOREIGN PATENT DOCUMENTS

CN 1345590 * 4/2012

* cited by examiner

*Primary Examiner* — Michael Meller

(57) ABSTRACT

A natural pharmaceutical preparation for treating hypoproteinemia, includes at least one member selected from the group consisting of a drug of increasing human serum albium, a drug of improving and enhance immunity, a drug of treating hepatitis B, a drug of treating Hepatitis C, a drug of treating acquired immune deficiency syndrome (AIDS), a drug of treating Tuberculosis, a drug of treat Fibrosis, a drug of treating hydrothorax, a drug of easing pain, a drug of stopping diarrhea, a drug of arresting coughing, a drug of reducing inflammation, and a drug of increasing urine.

1 Claim, No Drawings

NATURAL PHARMACEUTICAL PREPARATIONS FOR INCREASING ALBUMIN

BACKGROUND OF THE PRESENT INVENTION

1. Field of Invention

The subject invention relates generally to a series of natural pharmaceutical preparations which can treat hypoproteinemia for increasing albumin. The preparations could be used to treat hypoproteinemia caused by hepatitis virus, human immunodeficiency virus (HIV), tubercle bacillus, liver fibrosis, tumor, peritonitis, ascites and so on, and still could treat viral and toxic hepatitis and its cirrhosis, acquired immune deficiency syndrome (AIDS) and tuberculosis.

2. Description of Related Arts

Human serum albumin is an important part of blood system, it accounts for 40%-60% of total plasma protein, its half live in plasm is 15-19 days approximately. The major functions of human serum albumin (HSA) are to bind and transporting a variety of endogenous and exogenous substances, and to maintain blood fliter pressure, and to clear free-bond, and to inhibit activity of blood platelet, and to prevent the clotting of blood and to regulate fliter pressure of artery.

There are many causes of lowered blood albumin, including shock, burn, polycythemia, hypoalbuminemia, nephrogenic, pulmonary infection, intra-abdominal infection, gastric cancer, intestinal cancer, liver cancers, viral (hepatitis A, B, C virus) or chemical liver damage, severe heart failure, Tuberculosis, acquired immune deficiency syndrome (AIDS), pleurisy, nephrotic syndrome, lupus nephritis, diabetic kidney disease, brain disorders, extravasated blood related lesions of the gastrointestinal tract, chronic pancreatitis, malignant hypertension and so on.

Human serum albumin and recombinant human growth hormone are effective against hypoproteinemia, some sort of natural drugs also have a certain role to rise blood albumin, including Ginseng, Cornu Cervipantotrichum, Cassia Bark, Medicinal Indianmulberry Root, Milkvetch Root, Solomonseal Rhizome, Barbary Wolfberry Fruit, Glossy Ganoderma. However, these natural drugs can not cure hypoproteinemia caused by chronic intrauterine change which include cirrhotic cscites, uberculous pleural effusion, nephrotic syndrome (NS) in a patient with diabetes mellitus, chronic pancreatitis and so on.

SUMMARY OF THE PRESENT INVENTION

An object of the present invention is to provide a seires of therapeutic preparations for hypoproteinemia, and further disclose their use in the prevention or treatment of related diseases of hypoproteinemia. The preparations of the invention comprise some herbs which have different effects, moreover, more than one having the same effect, the preparation has multi-effects and multi-targets in comprehensive treatment.

The subject invention consists of herbs which have different effects as below:

1. A class of herbs used to increase human serum albium, including Milkvetch Root, Virgate Wormwood Herb, Lightyellow Sophora Root, Indian Buead, Largehead Atractylodes Rhizome, Turtle Carapace, Vietnamese Sophora Root, Ginseng, Cornu Cervipaantotrichum, Cassia Bark, Medicinal Indianmulberry Root, Solomonseal Rhizome, Barbary Wolfberry Fruit and Glossy Ganoderma.

2. A class of herbs used to improve and enhancing immunity, including Largehead Atractylodes Rhizome, Tree Peony Bark, Danshen Root, Vietnamese Sophora Root, Pseudoginseng Root, Common Yam Rhizome, Tamariskoid Spikemoss Herb, Solomonseal Rhizome, Glossy Ganoderma, Heartleaf Houttuynia Herb, Virgate Wormwood Herb, Lightyellow Sophora Root, Indian Buead, Milkvetch Root, Turtle Carapace, Toad Skin, Spreading Hedyotis Herb, Red Paeony Root, Drying Rehmannia Root, Prepared Rehmanniae Root, Scorpion, Pilose Asiabell Root, Zedoray Rhizome, Oriental Waterplantain Rhizome, Barbary Wolfberry Fruit or their combinations.

3. A class of herbs used to treat hepatitis B, including Common Leafflower Herb, Polyporus, Lightyellow Sophora Root, Javan Waterdropwort Herb, Vine Tea Leaf, Coriolus Versicolour Sporphore, Spreading Hedyotis Herb, Giant Knotweed Rhizome, Danshen Root and Linearstripe Rabdosia Herb or their combination.

4. A class of herbs used to treat Hepatitis C, including Silybum Marianum Fruit, Lightyellow Sophora Root, Spreading Hedyotis Herb, Giant Knotweed Rhizome, Danshen Root and Linearstripe Rabdosia Herb, Red Paeony Root, Zedoray Rhizome, Common Creenbrier Tuber or their combination.

5. A class of herbs used to treat acquired immune deficiency syndrome (AIDS), including Liquorice Root, Milkvetch Root, Medicine Terminalia Fruit, Japanese Honeysuckle Flower, Black Nightshade Herb, bark of white mulberry root, Snakegourd Root, Virgate Wormwood Herb, Common Selfheal Fruit-Spike, Asiatic Pennywort Herb, Barbed Skullcup Herb, Turtle Carapace, Danshen Root, Milkvetch Root, Lightyellow Sophora Root, Scorpion, Chinese Taxillus Herb, Colored Mistletoe Herb, Glandularstalk St. Paulswort Herb, Chinese Thorowax Root, Centipede and Toad Skin or their combination.

6. A class of herbs used to treat Tuberculosis, including Milkvetch Root, Danshen Root, Vietnamese Sophora Root, Liquorice Root, Chinese Taxillus Herb, Colored Mistletoe Herb, Lightyellow Sophora Root, Toad Skin, Scorpion, Centipede and Zedoray Rhizome or their combination.

7. A class of herbs used to treat Fibrosis, including Danshen Root, Liquorice Root, Lightyellow Sophora Root, Szechuan Lovage Rhizome, Cow-bezoar, Coriolus Versicolour Sporphore, Ginkgo Leaf, Silybum Marianum Fruit, Pseudoginseng Root, Beautiful Phyllodium Twig and Leaf or their combination.

8. A class of herbs used to treat hydrothorax, including Turtle Carapace, Toad Skin, Danshen Roots, Virgate Wormwood Herb or their combination.

9. A class of herbs used to ease pain, including Scorpion, Common Creenbrier Tuber, Common Yam Rhizome, Centipede, Perilla Fruit or their combination.

10. A class of herbs used to stop diarrhea, including Chinese Pulsatilla Root, Ash Bark, Amur Barberry Root, Lightyellow Sophora Root, Purslane Herb or their combination.

11. A class of herbs used to arrest coughing, including Perilla Fruit, Pilose Asiabell Root, Liquorice Root, Spreading Hedyotis Herb or their combination.

12. A class of herbs used to reduce inflammation, including Virgate Wormwood Herb, Golden Thread, Black Nightshade Herb, Perilla Fruit, Pseudoginseng Root or their combination.

13. A class of herbs used to increase urine, including Largehead Atractylodes Rhizome, Chinese Taxillus Herb, Colored Mistletoe Herb or their combination.

The person skilled in the relevant field of technology can choose the above-mentioned class of herbs and composition prepared with herbs to prepare preparations according to diseases and symptoms, and carries out by known public technology of preparation. The present invention discloses corresponding preferred preparation groups and preparation embodiments. The English Name and Scientific Name of medical herbs selected in the invention were shown in table 1, English names comply to "China Approved Drug Names" that based on the effective parts of herbs and animals.

TABLE 1

Directory of natural drugs preferred in the invention

| NO. | English Name | Scientific Name. |
|---|---|---|
| 1 | Medicinal Indianmulberry Root | *Morinda officinalis* How. |
| 2 | Spreading *Hedyotis* Herb | *Hedyotis diffusa* Willd. |
| 3 | Common *Bletilla* Tuber | *Bletilla striata* (Thunb.) Reichb. F. |
| 4 | Largehead *Atractylodes* Rhizome | *Atractylodes macrocephala* Koidz. |
| 5 | Chinese *Pulsatilla* Root | *Pulsatilla chinensis* (Bge.) Regel. |
| 6 | Barbed Skullcup Herb | *Scutellaria barbata* D. Don. |
| 7 | Turtle Carapace | *Trionyx sinesis* Wiegmann. |
| 8 | *Atractylodes* Rhizome | 1. *Atractylodes lancea* (Thunb) DC. 2. Atractylodes chinensis (DC.) Koidz. |
| 9 | Chinese Thorowax Root | 1. *Bupleurum chinense* DC. 2. *Bupeurum scorzonerifolium* Willd. |
| 10 | Toad Skin | 1. *Bufo bufo gargarizans* Cantor. 2. *Bofo melanostictus* Schneider |
| 11 | Toad Venom | 1. *Bufo bufo gargarizans* Cantor. 2. *Bofo melanostictus* Schneider |
| 12 | Red Paeony Root | 1. Paeonia lactiflora Pall. 2. Paeonia veitchii Lynch. |
| 13 | Szechuan Lovage Rhizome | *Ligusticum chuanxiong* Hort. |
| 14 | Danshen Root | *Slauia miltiorrhiza* Bge. |
| 15 | Pilose Asiabell Root | 1. *Codonopsis pilosula* (Franch.) Nannf. 2. *Codonopsis pilosula* Nannf. var. *modesta* (Nannf.) L. T. Shen. 3. *Codonopsis tangshen* Oliv. |
| 16 | *Coriolus Versicolour* Sporphore | *Coriolus versicolour* (L. ex Fr.) Quel. |
| 17 | Zedoray Rhizome | 1. *Curcuma phaeocaulis* Valeton. 2. Curcuma Kwangsiensis S. G, Lee et C. Liang. 3. *Curcuma wenyujin* Y. H. Chen et C. Ling. |
| 18 | Fourstamen Stephania Root | *Stephaniae Tetrandra* S. Moorre. |
| 19 | Indian Buead | *Poria cocos* (Schw.) Wolf. |
| 20 | Liquorice Root | 1. *Glycyrrhiza uralensis* Fisch. 2. Glycyrrhiza inflata Bat. 3. *Glycyrrhiza glabra* L. |
| 21 | Drying *Rehmannia* Root | *Rehmannia glutinosa* (Gaertn.)Libosch. ex Fisch. Et Mey. |
| 22 | Barbary Wolfberry Fruit | *Lycium barbarum* L. |
| 23 | Bulb of Edible Tulip | 1. *Tulipa edulis* (Miq.)Baker. 2. *Tulipa iliensis* Regel. |
| 24 | Medicine *Terminalia* Fruit | 1. *Terminalia chebula* Retz. 2. *Terminalia chebula* Retz. var. *tomentella* Kurt. |
| 25 | Colored Mistletoe Herb | *Viscum coloratum* (Komar.)Nakai |
| 26 | Giant Knotweed Rhizome | *Polygonum Cuspidatum* Sieb. et Zucc. |
| 27 | Solomonseal Rhizome | 1. *Polygonatum kingianum* Coll. 2. *Polygonatum cyrtonema* Hua |
| 28 | Golden Thread | 1. *Coptis chinensis* Franch. 2. *Coptis deltoidea* C. Y. Cheng et Hsiao. 3. *Coptis teeta* Wall. |
| 29 | Milkvetch Root | 1. *Astragalus membranaceus* (Fisch.) Bge. var. *mongholicus* (Bge.) Hsiao. 2. *Astragalus membranaceus* (Fisch.) Bge. |
| 30 | Asiatic Pennywort Herb | *Centella asiatica* (L.) Urb. |
| 31 | Japanese Honeysuckle Flower | *Lonicera japonica* Thunb. |
| 32 | Tamariskoid Spikemoss Herb | 1. *Selaginella tamariscina* (Beauv.) Spring. 2. *Selaginella pulvinata* (Hook. Et Grev.) Maxim. |
| 33 | Lightyellow *Sophora* Root | *Sophora flavescens* Ait. |
| 34 | Glossy *Ganoderma* | 1. *Ganoderma lucidum* (Leyss. Ex Fr.) Karst. 2. *Ganoderma sinensis* Zhao, Xu et Zhang. |
| 35 | Black Nightshade Herb | *Solanum nigrum* L. |
| 36 | Cornu Cervipantotrichum | 1. *Cervus nippon* Temminck. 2. *Cervus elaphus Linnaeus.* |
| 37 | Purslane Herb | *Portulaca oleracea* L. |
| 38 | Tree Peony Bark | *Paeonia suffruticosa* Andr. |
| 39 | Oyster Shell | 1. *Ostrea gigas* Thuberg. 2. *Ostrea talienwhanensis* Crosse. 3. *Ostrea rivularis* Gould |
| 40 | Cow-bezoar | *Bos taurus domesticus* Gmelin |

TABLE 1-continued

Directory of natural drugs preferred in the invention

| NO. | English Name | Scientific Name. |
|---|---|---|
| 41 | Beautiful *Phyllodium* Twig and Leaf | *Phyllodium pulchellum* (L.)Desv. |
| 42 | Ash Bark | 1. *Fraxinus rhynchophylla* Hance. 2. *Fraxinus chinensis* Roxb. 3. *Fraxinus szaboana* Lingelsh. 4. *Fraxinus stylosa* Lingelsh. |
| 43 | Sweet Wormwood Herb | *Artemisia annua* L. |
| 44 | Scorpion | *Buthus martensii* Karsch |
| 45 | *Ginseng* | *Panax ginseng* C. A. Mey. |
| 46 | *Cassia* Bark | 1. *Cinnamomum cassia* Presl. 2. *Cinnamomum cassia* Presl var. *macrophyllum* Chu |
| 47 | Common Creenbrier Tuber | *Sparganium stoloniferum* Buch.-Ham. |
| 48 | Pseudoginseng Root | *Panax notoginseng* (Burk.) F. H. Chenmn. |
| 49 | Chinese *Taxillus* Herb | *Taxillus chinensis* (DC.)Danser. |
| 50 | Indian Iphigenia Bulb | 1. *Cremastra appendiculata* (D. Don) Makino. 2. *Pleione bulbocodioides* (Franch.) Rolfe. 3. *Pleione yunnanensis* Rolfe. |
| 51 | Vietnamese Sophora Root | *Sophorae Tonkinensis* Gagnep. |
| 52 | Common Yam Rhizome | *Dioscorea opposita* Thunb. |
| 53 | Prepared Rehmanniae Root | *Rehmannia glutinosa* Libosch. |
| 54 | *Silybum Marianum* Fruit | *Silybum marianum* (L.) Gaertn. |
| 55 | Javan Waterdropwort Herb | *Oenanthe javanica* (Bl.) DC. |
| 56 | Leech | 1. *Whitmania pigra* Whitman. 2. *Hirudo nipponica Whitmania*. 3. *acranulata* Whitman |
| 57 | Snakegourd Root | 1. *Trichosanthes Kirilowii* Maxim. 2. *Trichosanthes rosthornii* Harms. |
| 58 | Centipede | *Scolopendra subspinipes mutilans* L. Koch. |
| 59 | Linearstripe Rabdosia Herb | *Lophanthoidis Isodon striatus* (Benth.) Kudo. |
| 60 | Glandularstalk St. Paulswort Herb | *Siegesbeckia pubescens* Makino. |
| 61 | Common Selfheal Fruit-Spike | *Prunella vulgaris* L. |
| 62 | Vine Tea Leaf | *Am pelopsis grossedentata* (Hand-Mazz) W. T. Wang. |
| 63 | Figwort Root | *Scrophularia ningpoensis* Hemsl. |
| 64 | Virgate Wormwood Herb | 1. *Artemisia scoparia* Waldst. et Kit. 2. *Artemisia capillaris* Thunb. |
| 65 | *Ginkgo* Leaf | *Ginkgo bilobe* L. |
| 66 | Heartleaf *Houttuynia* Herb | *Houttuynia cordata* Thunb. |
| 67 | Oriental Waterplantain Rhizome | *Alisma orientalis* (Sam.) Juzep. |
| 68 | Common Leafflower Herb | *Phyllanthus urinaria* Linn. |
| 69 | *Polyporus* | *Polyporus umbellatus* (Pers) Fires. |
| 70 | Bamboo Shavings | 1. *Phyllostachyl nigra* (Lodd. ex Lindl.) Munro var. *henonis* (Mitf.) Stapf et Rendle. 2. *Bambusa tuldoides* Munro. 3. *Sinocalamus beecheyanus* (Munro) McClure var. *pubescens* P. F. Li. |
| 71 | *Perilla* Fruit | *Perilla furtescens* (L.) Britt. |

The natural pharmaceutical preparations involved in the invrention come from powder of the effective parts of herbs and animals or their extract or their mixture. The standard of common medicinal herbs and animals in subject invention all base on Chinese Pharmacopoeia, effective parts of herbs and animals outside Chinese Pharmacopoeia are used with English name and scientific name that were described in the invention. The higher quality Medicinal herbs and animals in Chinese Pharmacopoeia are chosen from their genera and species, i.e. Milkvetch Root selected in subject preparation come from *Astragalus* membranaceus (Fisch.) Bge. and *Astragalus* membranaceus Bge. var. mongholicus (Bge.) Hsiao. Medicinal herbs and animals used in subject invention all could be replaced by other herbs and animals in the same genera and species, moreover, some one which has the same effect could be added into preparation.

It is well known that many sorts of natural drugs exert the same effect in the treatment. Toad Venom and Toad Skin have similar effects, but Toad Venom is higher toxic. Croton Seed has high-activity to kill uberculosis bacterium, but it has high toxicity, too. Nux Vomica seed has excellent Analgesic effect but toxicity is also high. These herbs that have high toxicity are selected but not optimal selection in subject invention. The number of species of herbs and animals in the invention were optimized as 10-60.

A person skilled in the relevant field of technology could design and formulate a series of preparations on the basis of natural drugs in the invention. The invention takes some preferred preparations for instance, but it is not limited to the several above-mentional preparations. Citing is as follows:

Preparation 1 which can be used to treat hepatitis and related complications: Milkvetch Root, Common Leafflower Herb, Japanese Honeysuckle Flower, Toad Skin, Lightyellow Sophora Root, Vietnamese Sophora Root, Spreading Hedyotis Herb, Virgate Wormwood Herb, Giant Knotweed Rhizome, Tamariskoid Spikemoss Herb, Red Paeony Root, Snakegourd Root, Danshen Root, Turtle Carapace, Oyster Shell, Heartleaf Houttuynia Herb, Indian Iphigenia Bulb, Common Yam Rhizome, Pseudoginseng Root, Zedoray Rhizome, Common Creenbrier Tuber, Medicinal Indianmulberry Root, Chinese Taxillus Herb, Prepared Rehmanniae Root, Oriental Waterplantain Rhizome, Indian Buead, Centipede, Scorpion, and Liquorice Root.

Preparation 2 which can be used to treat tuberculosis and hepatitis: Heartleaf Houttuynia Herb, Toad Skin, Common Leafflower Herb, Golden Cypress, Solomonseal Rhizome, Indian Iphigenia Bulb, Barbed Skullcup Herb, Chinese Taxillus Herb, Tree Peony Bark, Bark of Boxthorn Root, Angelica Archangelica Root, White Paeony Root, Danshen Root, Zedoray Rhizome, Turtle Carapace, Tamariskoid Spikemoss Herb, Snakegourd Root, Barbary Wolfberry Fruit, Perilla Fruit, Common Creenbrier Tuber, Oyster Shell, Indian Buead, Largehead Atractylodes Rhizome, Scorpion and Centipede.

Preparation 3 which can be used to treat AIDS, tuberculosis, hepatitis, opportunistic infection: Heartleaf Houttuynia Herb, Japanese Honeysuckle Flower, Toad Skin, Lightyellow Sophora Root, Vietnamese Sophora Root, Golden Cypress, Barbed Skullcup Herb, Common Leafflower Herb, Chinese Taxillus Herb, Tree Peony Bark, Liquorice Root, White Paeony Root, Danshen Root, Zedoray Rhizome, Turtle Carapace, Perilla Fruit, Indian Buead, Largehead Atractylodes Rhizome, Scorpion, Centipede, Pseudoginseng Root, Prepared Rehmanniae Root, Black Nightshade Herb, Tamariskoid Spikemoss Herb, Barbary Wolfberry Fruit, Milkvetch Root and white mulberry root-bark.

Three above-mentioned preferred preparations could treat different indications, the content of natural drugs in preparation are equal. Their daily dose are 10 gram per day in adults (for extract of preparation: 2 gram/day). In order to reduce side effects of each natural drug, their proportion was equal in the invention. several herbs have the same effect were selected so as to reduce drug-resistance.

The medicinal herbs of the present invention after grinding may be made into common preparations, including capsule, tablet and other forms. The natural herbs in the preparation can also be mixed with extract obtained from a part of powder or herb or animal by conventional methods, then it is used to fill capsule or to press tablet or to prepare other forms.

The preparation in subject invention is made from powder or extract of herbs directly. Its efficacy is determined through animal experiments and clinical observation.

In general, the pharmaceutical composition is prepared by admixing the active ingredient to one or more carrier(s). Preparation in subject invention can make up compound together with chemical and biological drugs. Preparation in subject invention includes pill, powder, medicinal extract, electuary, tablet, capsule, chewable tablet, syrup, and oral solution.

Related carriers/adjuvants in subject invention are Starch, talc, sugar, Jiao flavor agent, soluble starch, dextrin class, ethanol, polyethylene glycol, Propylene glycol, vegetable oil, gelatin, Tween etc. and other surfactants, and include stuffing agent, for example, Starch, sugar; adhesion agent, as for example, cellulose derivatives, alginate, gelatin and polyvinylpyrrolidone; Wetting agents, such as glycerol; disintegrating agents, as for example, agar, calcium carbonate and sodium bicarbonate; Absorption enhancers, for example, quaternary ammonium compounds; surface active agent, such as 16 triacontanol; adsorption carrier, as for example, kaolin clay and soap; lubricants, as for example, talc, calcium and magnesium stearate and polyethylene glycol, etc. In addition other adjuvants can be filled into natural herbs that can inhance endogenous albumin, such as Flavor enhancers, sweeteners, and others.

Preparations in the present invention will be used in the prevention or treatment of hypoproteinemia and its related diseases. Above-mentioned hypoalbuminemia include hepatogenic ascites and pleural effusion of non-hepatic immunogenicity, infection, edema. The related diseases as described include hepatitis and liver fibrosis, tuberculosis and pleurisy, pulmonary tuberculosis, AIDS and opportunistic infections, nephrotic syndrome or diabetic nephropathy, lupus nephritis, brain diseases, gastrointestinal stasis disease, chronic pancreatitis, a large number of blood loss, burns, trauma, malignant hypertension and others.

Many reasons which cause hypoalbuminemia can be summarized as liver immunogenicity and non-divided Hepatogenic. But the wish to improve hypoalbuminemia involve the function of albumin synthesis in liver. Hepatogenic hypoalbuminemia's major causes come from virus (A, B and C hepatitis virus) or toxic chemical substances (organics and inorganics affecting liver function such as alcohol), and liver cancer. The causes can trigger the liver cell injury, followed by the slow formation of hepatic fibrosis, albumin synthesis or excretion dysfunction in hepatic cells, leading to ascites eventually.

Many reasons cause non-hepatogenic hypoalbuminemia, for example, a virus or bacterial infection of extrahepatic organs or physical factors such as burns, trauma, blood loss, all of them can cause a extrahepatic decline of serum albumin.

To sum up, hypoalbuminemia and its related diseases prevented or treated in the subject invention are liver pathogenic and non-Hepatogenic hypoalbuminemia, such as liver fibrosis, tuberculosis, AIDS, nephrotic syndrome, lupus kidney inflammation, diabetes, kidney disease, brain disorders, gastrointestinal stasis disease, chronic pancreatitis, a large number of blood loss, burns, trauma, malignant hypertension, and so on. The present invention is described in some examples in details. The following examples can make the person skilled in this field more fully understand this invention, rather than limit the scope of protection of this invention.

DETAILED DESCRIPTION OF THE PREFERRED EMBODIMENT

Example 1

Impact of Preparation 1 on Content of Serum Albumin in Mice

The mice were divided into 4 groups (n=10), i.e., normal control group, high-dose group (5200 g/kg), moderate-dose group (2600 g/kg), low-dose group (1300 g/kg), administered with preparation 1 for 3 weeks intragastrically. The content of serum albumin in each group was measured after administration 1 week, 2 week, 3 week respectively (Table 2).

TABLE 2

Impact of Preparation 1 on Content of Serum Albumin in Mice ($\bar{x} \pm s$)

| Groups | n | Dose (mg/kg) | After 1 week ALB (g/L) | GLB (g/L) | TP (g/L) | After 3 weeks ALB (g/L) | GLB (g/L) | TP (g/L) |
|---|---|---|---|---|---|---|---|---|
| Normal control | 10 | — | 29.0 ± 2.2 | 28.0 ± 1.3 | 57.9 ± 2.9 | 29.7 ± 1.1 | 46.9 ± 2.3 | 76.6 ± 2.6 |
| Preparation 1 | 10 | 5200 | 27.8 ± 1.7 | 28.5 ± 2.2 | 56.3 ± 2.7 | 30.1 ± 0.9 | 46.4 ± 1.5 | 76.5 ± 1.9 |
| Preparation 2 | 10 | 2600 | 30.8 ± 1.2* | 26.1 ± 2.5 | 56.9 ± 2.9 | 31.1 ± 1.4* | 45.2 ± 2.7 | 76.4 ± 2.0 |
| Preparation 3 | 10 | 1300 | 29.4 ± 2.1 | 26.9 ± 2.8 | 56.3 ± 2.4 | 30.1 ± 1.4* | 44.6 ± 3.2 | 75.5 ± 3.3 |

Compared with normal group: *p < 0.05.

The results of experiment suggested that preparations in invention could increase serum albumin in mice with certain dosage range, but preparation 1 of high dose had no activity.

Example 2

Impact of Preparations in the Invention on Content of Hepatogenic Serum Albumin, Ascites, Fibrosis Associated Substance in Rat $CCl_4$-induced liver injury: the method for establishing rat model of liver cirrhosis come from reference literature. In the first week, rats were given drinking water containing penobarbital (35%), which is induced-period. To begin from second week, $CCl_4$-olive oil solution (40%) was subcutaneously injected into the rat with dose 2 mL/kg twice a week, administrated subcutaneously for 9 weeks with doubling first dose, then made a judgment on whether ascites exsited according to abdominal circumference and puncture.

The rats with ascites were randomly divided into groups, i.e. Model group and Positive group (colchicine 0.233 mg/kg) by weight. Rats in each group were administrated for 4 weeks intragastrically. One hour after last administration, rat was anesthetized with aether, cut abdominal cavity open, examined whether ascites exsited, used $\chi^2$ test to calibrate the rate of ascites reduction.

And blood samples were drawn from abdominal aorta to prepare serum, indexes were determined according to requirements of Kit as below: alanine amiotransferase (ALT), aspartate aminotransferase (AST), alkaline phosphatase (ALP), total protein (TP), albumin (ALB), globin (GLB), hyaluronidase (HA), laminin (LN), type III procollagen (PC III). While a portion of liver of rat was cut for determining concentration of Proline. Finally, the part of liver was fixed with paraformaldehyde (10%) for pathological examination. The results are shown in the Table 3, 4, 5 as below:

TABLE 3

Impact of Preparation on Content of Serum Albumin in Liver Injured Rat by $CCl_4$

| Groups | Dose mg/kg | n | TP g/L | ALB g/L | GLB g/L | ALB/GLB |
|---|---|---|---|---|---|---|
| Normal control group | — | 10 | 52.0 ± 4.5 | 38.1 ± 3.0 | 13.9 ± 6.5 | 3.5 ± 2.2 |
| Negative control group | — | 10 | 54.0 ± 3.4 | 30.8 ± 6.1** | 23.2 ± 7.6** | 1.5 ± 0.7* |
| Colchicine group | 0.23 | 10 | 55.2 ± 3.9 | 38.1 ± 5.6* | 17.1 ± 7.7 | 2.8 ± 1.6* |
| Preparation 1 group | 2000 | 10 | 55.3 ± 2.9 | 37.5 ± 2.8** | 17.8 ± 3.1 | 2.2 ± 0.5* |
| Preparation 2 group | 2000 | 10 | 56.6 ± 9.9 | 37.2 ± 2.3** | 19.3 ± 10.8 | 3.4 ± 3.6 |
| Preparation 3 group | 2000 | 10 | 52.9 ± 4.3 | 36.8 ± 4.2* | 16.1 ± 4.6* | 2.5 ± 0.8* |
| Extract of Preparation 1 | 200 | 10 | 62.8 ± 3.9 | 26.8 ± 4.7** | 36.0 ± 5.2 | 0.8 ± 0.2** |

Compared with Normal control group: *p < 0.05, **p < 0.01;
Compared with Negative control group: *p < 0.05, **p < 0.01.

TABLE 4

Impact of Preparations on ascites in CCL4-induced hepatic fibrosis in rats

| Groups | Dose mg/kg | Normal Animal n | Animal with ascites n | Incidence % | x2 值 | P 值 |
|---|---|---|---|---|---|---|
| Normal control group | — | 10 | 0 | 0 | 16.2 | <0.01 |
| Negative control group | — | 10 | 10 | 100 | | |
| Colchicine group | 0.23 | 10 | 5 | 50 | 4.27 | <0.05 |
| Preparation 1 group | 2000 | 10 | 4 | 40 | 5.95 | <0.05 |
| Preparation 2 group | 2000 | 10 | 4 | 40 | 5.95 | <0.05 |
| Preparation 3 group | 2000 | 10 | 5 | 50 | 4.27 | <0.05 |
| Extract of Preparation 1 | 400 | 10 | 1 | 10 | 5.95 | <0.05 |

TABLE 5

Impact of Preparations on HA, PCIII, LN in CCL4-induced hepatic fibrosis in rats (n = 10, $\bar{x} \pm s$)

| Groups | Dose mg/kg | HA ng/ml | PCIII ng/ml | LN ng/ml | HPRO mg/g (Liver Weight) |
|---|---|---|---|---|---|
| Normal control group | — | 106.6 ± 19.6 | 16.7 ± 3.4 | 35.3 ± 5.3 | 0.23 ± 0.004 |
| Negative control group | — | 240.5 ± 137.3** | 22.6 ± 4.9** | 54.7 ± 13.9** | 0.43 ± 0.11** |
| Colchicine group | 0.23 | 172.9 ± 47.7 | 17.3 ± 4.2* | 43.2 ± 13.8 | 0.29 ± 0.08** |
| Preparation 1 group | 2000 | 202.2 ± 118.7 | 16.1 ± 4.1** | 33.4 ± 11.1** | 0.32 ± 0.08* |
| Preparation 2 group | 2000 | 142.2 ± 62.4 | 10.8 ± 2.9** | 30.0 ± 10.6** | 0.31 ± 0.08* |
| Preparation 3 group | 2000 | 140.5 ± 53.1* | 11.2 ± 3.9** | 34.7 ± 13.3** | 0.29 ± 0.09** |
| Extract of Preparation 1 | 2000 | 122.16 ± 66.1** | 22.6 ± 3.3** | 48.9 ± 7.7** | 2.9 ± 0.9** |

Compared with Normal control group: *p < 0.05, ** p < 0.01;
Compared with Negative control group: *p < 0.05, ** p < 0.01.

The results has shown that the preparations in subject invention can increase serum albumin and treat hepatic fibrosis and inflammation.

Example 3

Effect of Preparation 1, 2, 3 on Load Level of HBV

HBV load level: LongYan Shelducks, 3 days old, were drawn blood from jugular vein on next day, separated and prepared serum, measured DHBV-DNA with PCR, then ducks congenitally infected with HBV were selected for experiments. Tested drugs: Preparation 1, 2, 3, dose: 2000 g/kg, oral administration. Set up negative control group by water instead of medicine. Lamivudine (3TC) was used in positive control group, oral administration, a course of treatment included 21 days. Eight duckes in each group. Venous blood was collected on 0 day (collected before administration of cyclophosphamide) and on 7th day (T7), 14th day (T14), 21th day (T21), and serum prepared was stored in −70 C.

Detection Method for DHBV-DNA: Use above-mentioned serum to spot on membrane for detecting total serum DHBV-DNA level, according to manual of nick translation kit, label DHBV-DNA probe with 32P, carry out Dot-Blot DNA Hybridisation assay, the relevant results are showed in the autoradiography assay, measure OD490 nm absorbance with a microplate reader, calculate density of DHBV-DNA in serum. The statistical analysis to virus load is shown in Table 6.

TABLE 6

Inhibition effects of preparations on DHBV-DNA in duck

| Groups | Duckes (n) | Dose (mg/kg) | OD490 Absorbance T0 | T7 | T14 | T21 |
|---|---|---|---|---|---|---|
| Normal control group | 8 | | 0.62 ± 0.59 | 0.65 ± 0.38 | 0.60 ± 0.36 | 0.76 ± 0.55 |
| 3TC group | 8 | 20 | 0.95 ± 0.61 | 0.00 ± 0.00*** | 0.08 ± 0.03*** | 0.11 ± 0.15** |
| Preparation 1 | 8 | 2000 | 0.65 ± 0.28 | 0.37 ± 0.26* | 0.31 ± 0.22* | 0.36 ± 0.25** |
| Preparation 2 | 8 | 2000 | 0.75 ± 0.33 | 0.39 ± 0.29 | 0.42 ± 0.36 | 0.45 ± 0.13* |
| Preparation 3 | 8 | 2000 | 0.94 ± 0.84 | 0.52 ± 0.22 | 0.58 ± 0.23 | 0.34 ± 0.24* |

Compared with Normal control group: *p < 0.05, **p < 0.01;
Compared with Negative control group: *p < 0.05, **p < 0.01.

Example 4

Effect of Preparation 1 on Serum Albumin in Intra-Abdominal Infection of Rats

The mice are divided into 6 groups (n=10), i.e., Normal control group, Negative control group, Positive control group (Panaxoside), in the remaining 3 groups, rats were fed with preparation 1 through intragastric administration for 6 days. Under anesthesia by diethyl ether, abdominal cavity of mice were cut open, experimental staff stick a puncture on appendices with needle to cause it infected, then sew up abdominal wound. Continue administration after surgery, animals were executed for collecting their blood to measure serum albumin levels, results are listed in Table 7.

TABLE 7

Effect of Preparation 1 on Serum Albumin in the Rats with Intra-abdominal Infection

| Groups | Dose (mg/kg) | n | ALB(g/L) |
|---|---|---|---|
| Normal control group | | 10 | 28.52 ± 2.95 |
| Negative control group | | 10 | 23.28 ± 4.95## |
| Panaxoside | 30 | 10 | 29.64 ± 2.29** |
| Preparation 1 | 2000 | 10 | 31.42 ± 2.96**# |

TABLE 7-continued

Effect of Preparation 1 on Serum Albumin in the Rats with Intra-abdominal Infection

| Groups | Dose (mg/kg) | n | ALB(g/L) |
|---|---|---|---|
| Preparation 1 | 1000 | 10 | 29.85 ± 2.79** |
| Preparation 1 | 500 | 10 | 29.59 ± 3.17** |

Compared with Normal control group: *p < 0.05, **p < 0.01;
Compared with Negative control group: *p < 0.05, **p < 0.01.

Preparation 1 and its extract significantly can inhibit the reduction of content of serum albumin in rat with Infectious Peritonitis. All results suggested that preparation 1 can be used as an agent for treating non hepatic lowered blood albumin.

Example 5

Anti-Tubercle Bacillus Assay of Preparation 2 and Preparation 3

5.1. Anti-Tubercle Bacillus Assay

Anti-tubercle bacillus assay is tested in vivo. C57BL/6 mice infected with H37Rv Tubercle Bacillus are divided into 6 groups (n=15), one is normal control group, another is positive control group (INH: 25 mg/kg), in other groups, preparations was added into mice's feed, animals are administrated consecutive 16 weeks.

Experimental staff Killed 5 mice at the 2nd, 4th, 16th week, obtained lung and spleen, put them into 1 ml 7H9 media, grinded and converted them into 1.5 ml Ep tube, doubly diluted 10 times with 7H9 media, then Plated different dilutions onto 7H11 solid media plates for 4w at 37° C., counted tuberculosis colonys.

Calculation Formula: (initial number of clone×final broth volume×dilution factor $10^3 \times 2 \times 10$)+(initial number of clone colony×final broth volume×dilution factor $10^4 \times 2 \times 10$)+(initial number of clone colony×final broth volume×dilution factor $10^5 \times 2 \times 10$)/3

Take tissue for pathological examination, weight lung, Calculation Formula: (initial number of clone×final broth volume×dilution factor $10^3 \times 2 \times 10$)+(initial number of clone colony×final broth volume×dilution factor $10^4 \times 2 \times 10$)+(initial number of clone colony×final broth volume×dilution factor $10^5 \times 2 \times 10$)/3×initial organ weight/organ weight in treatment.

Count number of Lung bacterial or mouse spleen CFU of every mouse in each group, convert data in accordance with 1 g (CFU).

TABLE 8

Total Lung bacterical count converted to Mean lg (CFU ± SEM)

| Groups | n | Dose (mg/kg) | 2 w | 4 w | 16 w |
|---|---|---|---|---|---|
| Negative control Groups | 15 | | 6.88 ± 0.38 | 6.57 ± 0.20 | 5.56 ± 0.21 |
| INH | 15 | 25 | 6.12 ± 0.22* | 5.59 ± 0.20* | 2.77 ± 0.16* |
| Preparation 2 | 15 | 1000 | 6.41 ± 0.37 | 6.22 ± 0.33 | 4.92 ± 0.49* |
| Preparation 2 | 15 | 2000 | 6.58 ± 0.38 | 5.90 ± 0.21* | 5.17 ± 0.30* |
| Preparation 3 | 15 | 1000 | 6.37 ± 0.38 | 6.02 ± 0.30* | 4.84 ± 0.46* |
| Preparation 3 | 15 | 2000 | 6.20 ± 0.32* | 5.99 ± 0.28* | 5.76 ± 0.71 |

Compared with Negative control group: *p < 0.05

The results revealed that Preparation 2, 3 had inhibiting effects agaist Tubercle Bacillus, compared with normal control group, different results between these groups were statistical significance. It has been reported in the literature that lung infection is an important factor leading to low serum albumin. Hence, anti-Tubercle Bacillus effect of natural medicine is a real and fundamental root cause to treat low serum albumin caused by lung infection.

5.2 Anti Drug-Resistant Tubercle Bacillus Assay

Serum-Pharmacology Methods was used in the assay, C57BL/6 mice were injected with HRSE-resistant (Isoniazid, Rifampicin, Streptomycin, Ethambutol-resistant), HR-resistant (Isoniazid and Rifampicin), H-resistant (Isoniazid), R-resistant (Rifampicin) separately, they were divided into 5 groups including negative control group, positive control group (Isoniazid, 25 mg/kg), the remaining 3 groups were administrated with 1000, 2000, 4000 mg/kg continuously for 6 days respectively. The last administration after 2 hours, we respectively draw 20 µl from 5 mice in each group, mix them as working serum 100 µl. Taking 10 µl working serum which was added it into 90 µl 7H9 medium containing $9 \times 10^3$ CFU drug-resistance (i.e. H, R, HR or HRSE) or standard tubercle bacillus stain, named diluting 10% with serum. some parallel wells were set in each group. Take positive control group (Isoniazid, 25 mg/kg) following the same steps, the medium was 90 µl 7H9 (containing $9 \times 10^3$ CFU stain)+10 µl blank 7H9 per group, some parallel wells were set, after 5 days in 37° C., diluted sample in each tube doublely, expect dilution titer is $10^3$, plated final dilution of each tube on 7H9 solid medium, 4 weeks in 37° C., counted number of colonies.

Calculating formulas: the number of bacteria colony=(the number of bacteria colony per group per batch×Dilution Factor 1000+the number of bacteria colony in parallel well× Dilution Factor 1000)/2.

Inhibition rate=mean of specific bacteria colony in experimental groups−mean of specific bacteria colony in NS group/ mean of specific bacteria colony in NS group×100.

TABLE 9

Inhibition rate of serum containing Preparation (%)

| Groups | Dose (mg/kg) | H-resistance | R-resistance | HR-resistance | HRSE-resistance |
|---|---|---|---|---|---|
| NS | | — | — | — | — |
| INH | 25 | 0 | 72 | 67 | 21 |
| Composition 2 | 1000 | 0 | 0 | 0 | 0 |
| Composition 2 | 2000 | 0 | 0 | 22 | 67 |
| Composion 2 | 4000 | 0 | 0 | 22 | 47 |

The results indicated that preparation 2 had an inhibition effect on HRSE-resistance, also induced a trend of inhibiting HR-resisitance stain.

5.3 The Impact of Preparation 1, 2, 3 on Tuberculous Pleural Effusions and Serum Albumin After sensitizing with BCG for 42 days, guinea pig was administrated with preparations for 7 days, sensitized for 2 days continuously, then measured the level of Pleural Effusion, number of white blood cell and content of serum albumin

TABLE 10

The impact of Preparation 1, 2, 3 on Tuberculous pleural effusions and serum albumin in Guinea pigs

| Groups | Dose (mg/kg) | Number (n) | Exudates volumes (ml) | WBC (×109) | ALB (g/L) |
|---|---|---|---|---|---|
| Normal control | | 8 | — | — | 29.98 ± 1.82 |
| Negative control | | 8 | 2.3 ± 0.77 | 27.2 ± 7.56 | 26.94 ± 1.70## |
| Dexamethasone | 5 | 8 | 1.2 ± 0.44** | 19.1 ± 5.24* | 29.05 ± 3.49 |
| Preparation 1 | 2000 | 8 | 1.2 ± 0.59** | 19.2 ± 5.75* | 29.34 ± 3.03* |
| Preparation 2 | 2000 | 8 | 1.2 ± 0.52** | 19.0 ± 4.55* | 28.48 ± 1.70* |
| Preparation 3 | 2000 | 8 | 1.3 ± 0.50** | 19.6 ± 4.93* | 28.35 ± 0.97* |

Compared with Normal control group: *p < 0.05, **p < 0.01;
Compared with Negative control group: *p < 0.05, **p < 0.01.

The results indicated that Preparation 2 could significantly reduce level of Pleural Effusion, number of white blood cell, make content of serum albumin increase.

Example 6

Preparation 3 Anti-HIV Assay

Sixteen male rhesus monkeys, 3.5-7 kg weight, 4-8 years old, were provided by Guangdong Primate Experimental Center appearance health, no superficial lymph nodes enlargement in physical examination, examine the antibodies of Simian Type D Retrovirus (SRV) and Simian T-lymphotropic Virus Type I (STLV-I), tubercle bacillus and Shigella, all of results were negative.

SIVmac251—generous present form Ph.D Marx at Aaron Diamond AIDS Research Center, 12 monkeys were infected with 5 MID100 dose (1 ml, 5 times of 100% infection).

Animals were then selected and randomly divided into groups. Virus infection started at Jun. 19, 2008, after 71 days, administrated at Dec. 19, 2008. Sixteen Monkeys infected by virus are divided into 4 groups, i.e., low dose group (0.25 g/kg), middle dose group (0.5 g/kg) (an equivalent dose of herapeutic clinical use), high dose group (1 g/kg) and negative control. The tested compositions prepared into 25 ml suspension were used to administrate once per day and for 8 weeks. Infected monkeys were minitored after stopping treatment. All results of experimental groups were as same as that of control group. The "Before treatment" referred to the 71st day after infecting with SIVmac251, "Four weeks after beginning treatment" was 99th day, "Eight weeks after beginning treatment" was 127th day, "Twelve weeks after beginning treatment" (4 weeks after stopping treatment) was 155th day, "sixteen weeks after beginning treatment" (8 weeks after stopping treatment) was 183rd day.

Tests: routine blood, ranges for $CD_4^+$ and $CD_8^+$ lymphocyte subsets, $CD_4^+/CD_8^+$ lymphocyte ratio tested by flow cytometry, absolute $CD_4^+$ and $CD_8^+$ lymphocyte count, plasma viral load, lymph node biopsy.

TABLE 11

Comparison between oneself of plasma viral load of monkey before and after treatment in each group (log10)

| Groups | Dose mg/kg | Before treatment | After treatment (weeks) 4 | 8 | 12 | Stopping treatment (weeks) 8 |
|---|---|---|---|---|---|---|
| SIV negative control | | 4.50 | 4.84 ↑ 0.34 | 4.76 ↑ 0.25 | 4.82 ↑ 0.32 | 5.35 ↑ 0.85 |
| Preparation 3 | 1000 | 4.61 | 4.49 ↓ 0.12 | 4.83 ↑ 0.22 | 4.02 ↓ 0.59 | 3.99 ↓ 0.62 |
| Preparation 3 | 500 | 4.30 | 4.30 ↓ 0.01 | 3.84 ↓ 0.46 | 4.00 ↓ 0.30 | 3.27 ↓ 1.03 |
| Preparation 3 | 250 | 5.75 | 5.55 ↓ 0.20 | 5.55 ↓ 0.20 | 5.86 ↑ 0.11 | 6.31 ↑ 0.55 |

TABLE 12

Comparison between oneself's $CD_4^+$ and $CD_8^+$ lymphocyte subsets of monkey before and after treatment in each group

| Groups | Dose mg/kg | Before treatment | After treatment (weeks) 4 | 8 | Stopping treatment (weeks) 4 | 8 |
|---|---|---|---|---|---|---|
| SIV negative Control | | 0.60 | 0.68 ↑ 0.08 | 0.86 ↑ 0.27 | 0.6 0 | 0.87 ↑ 0.28 |
| Preparation 3 | 1000 | 0.95 | 1.15 ↑ 0.20 | 1.39 ↑ 0.44 | 1.14 ↑ 0.18 | 1.3 ↑ 0.35 |
| Preparation 3 | 500 | 0.78 | 0.74 ↓ 0.10 | 1.04 ↑ 0.26 | 0.82 ↑ 0.03 | 1.24 ↑ 0.46 |
| Preparation 3 | 250 | 0.83 | 1 ↑ 0.21 | 1.04 ↑ 0.21 | 0.93 ↑ 0.11 | 1.19 ↑ 0.36 |

Concluding from Table 11 and Table 12, the preparation could reduce plasm viral load to certain extent and maintain decline trend after stopping treatment and raise $CD_4^+$ and $CD_8^+$ lymphocyte. Due to fewer monkeys in the assay, Dynamic not statistical analysis to data is performed.

SIV and HIV's animal mode are not fully consistent, so some drugs that have better effect to HIV are not up too much to SIV, e.g., AZT (Zidovudine) is the first drug approved for use as a Nucleoside analog reverse transcriptase inhibitors and it is a very commonly used drug in HIV Clinical Trials, but it could not inhibited infection by SW.

Example 7

Treatment of Clinical Cases

The infectious clinical cases can be divided into 2 categories: one is the patients who used inventor's preparations while stopping other drugs, another is the patients who did not stop other drugs. The patients who was treated by inventor were mostly through a long illness. These patients all were treated with chemotherapy, and most of them have drug-resistant. A part of patients who were cured and improved did not rule out possibility of the co-treament of chemical drugs and herbs.

Clincal cases in the invention were treated with preparation formulations including dried medicinal herbs, namely their powder, and decoction.

7.1 Preparation 1 in the Treatment of Liver Fibrosis and Pleural Effusion

Three-eighteen months was clinical preparation 1's treatment cycle, patients in the case had been treated by some hospitals, but had no improvement to their Liver fibrosis and Pleural effusion. Treatment goals: reversing Fibrosis, reduce Pleural effusion, returning liver function to normal. The inventor has treat patients like this for 12 years. These patients's course of treatment were 3-15 months, 10 g per day, 2-3 times per day, they were administrated with preparation of decoction which was equal to crude drug 30 grams.

TABLE 13

Results of Preparation 1 in the Treatment of Liver Fibrosis and Pleural effusion

| Types | Number | Results |
|---|---|---|
| Liver fibrosis | 306 | 200 cases returned liver function to normal, 103 cases improved, 3 cases failed to respond |
| concurrent Pleural effusion | 206 | 189 cases disappeared, 13 cases improved, 4 cases failed to respond |

7.2 Preparation 1 in the Treatment of Hepatitis B and Related Complications

The inventor has treated patients with Hepatitis B for 10 years, most of them were treated with some drugs, but failed to respond. These patients' course of treatment were with the preparation 1, 3-15 months, 10 g per day, 2-3 times per day, results as below:

TABLE 14

Results of Preparation 1 in the Treatment of Hepatitis B and related Complications

| Types | Number | Results |
|---|---|---|
| Hepatitis B Virus | 507 | In the testing virus load of 231 cases, 79 cases normal, 100 cases decline, 52 cases no change. |
| Concurrent Liver fibrosis | 507 | 299 cases returned liver function to normal, 200 cases improved, 8 cases failed to respond |
| Concurrent Pleural effusion | 189 | 181 cases disappeared, 6 cases improved, 2 cases failed to respond |

7.3. Preparation 2 in the Treatment of Tuberculosis

Patients were began to treat with Tuberculosis in 1960, most of them had persistent fever were not cured by Infectious Diseases Hospital. These patients were treated with Preparation 2, course of treatment was 3-18 months, 10 g per day, 2-3 times per day, results as below:

TABLE 15

Results of Preparation 2 in the Treatment of Tuberculosis

| Types | Number | Results |
|---|---|---|
| Cavitary Pulmonary Tuberculosis | 769 | 299 cases: cavitary disappeared and no tuberculosis, 430 cases: lesion calcified, 30cases efficiency, 10 no efficiency. |
| Non-cavitary Pulmonary Tuberculosis | 1956 | 1500 cases cured, 360 cases improved significantly, 74 cases improved, 22 cases failed to respond |
| Bone Tuberculosis | 56 | 50 cases cured, 6 cases improved significantly |
| Lymphatic Tuberculosis | 1200 | 1000 cases cured, 156 cases improved significantly, 30 cases improved, 14 cases failed to respond |

7.4 Preparation 3 in the Treatment of Tuberculosis, Hepatitis and Thrush

Inventor began to treat people living with HIV in 1998, before treatment: all patients were diagnosed with AIDS, which was conformed by Communicable Disease Control, Clinical symptoms: diarrhea, weight loss, thrush, concurrent tuberculosis and so on. Treatment goals: diarrhea disappeared, weight back, tuberculosis and hepatitis virus inhibited, thrush cured. Treating with Preparation 3, course was 3-12 months, results are shown as below:

TABLE 16

Results of Preparation 3 in the Treatment of AIDS and related Complications

| Types | Number | Results |
|---|---|---|
| Weight Loss | 31 | 20 cases return to normal, 6 cases back, 5 cases no change |
| Concurrent Tuberculosis | 12 | 5 cases cured, 7 case failed |
| Concurrent Diarhea | 27 | 20 cases disappeared, 6 cases improved, 1 case failed |
| Concurrent Thrush | 15 | 12 cased cured, 3 failed |
| Working Ability Loss | 31 | 20 cases restored |
| Concurrent HCV infection | 21 | 7 cases turn negative, other 14 cases no feedback information |
| Not to adhere to preparation | 7 | 7 cases died |

Example 8

Preparations Preparation

8.1 Powder Preparation

Get dried natural herbs 1000 g, crushing into particles with a size of 100 meshes, beating the mixture until smooth, package: 3 g/bag or 0.5 g/capsule.

8.2 Decoction Preparation

According to Preparation 1, get dried natural herbs 1000 g, adding 1000 ml $H_2O$, heat it at 105° C. for 60 minutes, cool, centrifugal filtrate, mix centrifugal residue with 2000 ml $H_2O$, heat it at 105° C. for 60 minutes again, cool, centrifugal filtrate, mix 2 rounds of centrifuge supernatant, dilute it into 5000 ml, pack into 15 ml/bottle.

8.3 Extract Preparation

According to Preparation 1, get dried natural herbs 1000 g, add it into heating kettle containing 6000 ml Solvent (alcohol: $H_2O$=50:50), filtrate it, Spray drying. The extract could be prepared into capsule, granule, tablet and oral application liquid.

What is claimed is:

1. A pharmaceutical composition for treating hypoproteinemia comprising therapeutically effective amounts of Polyporus extract, light yellow sophora root extract, javan waterdropwort extract, coriolus versicolor extract, spreading hedyotis extract, giant knotweed rhizome extract, dan shen root extract, linearstripe rabdosia extract, red paeony root extract, zedoary rhizome extract, cassia bark extract, toad skin, milkvetch root extract, glossy gandoderma extract, colored mistletoe extract, ginkgo leaf extract, liquorice root extract, and barbed skullcap extract.

* * * * *